United States Patent
Mayer

[11] Patent Number: 6,126,651
[45] Date of Patent: Oct. 3, 2000

[54] MOTORIZED MOTION-CANCELING SUTURE TOOL HOLDER

[76] Inventor: Paul W. Mayer, 6290 SW. 92nd St., Miami, Fla. 33156-1866

[21] Appl. No.: 09/132,409

[22] Filed: Aug. 11, 1998

Related U.S. Application Data

[60] Provisional application No. 60/054,736, Aug. 11, 1997, and provisional application No. 60/074,656, Feb. 13, 1998.

[51] Int. Cl.[7] .................................................. A61B 17/00
[52] U.S. Cl. ................................. 606/1; 606/2; 606/138; 606/144; 606/167; 128/897; 227/2; 227/175.1
[58] Field of Search ............................... 606/1, 2, 10, 13, 606/32, 34, 41, 167; 128/139–150, 897, 898; 227/175.1, 2

[56] References Cited

U.S. PATENT DOCUMENTS

| | | |
|---|---|---|
| 463,753 | 11/1891 | Connett . |
| 850,779 | 4/1907 | Peacock . |
| 2,580,964 | 1/1952 | Skaller . |
| 2,601,564 | 6/1952 | Smith . |
| 4,266,548 | 5/1981 | Davi . |
| 4,553,544 | 11/1985 | Nomoto et al. . |
| 4,803,984 | 2/1989 | Narayanan et al. . |
| 4,841,888 | 6/1989 | Mills et al. . |
| 4,878,494 | 11/1989 | Phillips et al. . |
| 5,254,113 | 10/1993 | Wilk . |
| 5,591,179 | 1/1997 | Edelstein . |

*Primary Examiner*—Linda C. M. Dvorak
*Assistant Examiner*—Bryan K. Yarnell
*Attorney, Agent, or Firm*—Browdy and Neimark

[57] ABSTRACT

An apparatus for open-heart surgery includes a suture-needle holding tip (10) or a stapler and a handle (100). The tip is driven to oscillate relative to the handle in the same motion as the surface of the heart, which is being operated on. This cancels the motion of the heart, effectively stopping it, so that the surgeon (S) need not compensate for heart beats. The tip can grasp or release the needle (N) with a mechanism (300) under control of a switch (330) through a flexible cable 120. Independently, a drive mechanism 200 causes a cam (230) to be turned by a motor 213 for driving the needle-holding tip by means of a flexible cable 120. The cam is shaped so that the pattern of the platform oscillation follows the beating heart's motion. A momentary-contact switch triggers a pacer, which paces the heart to beat in synchrony with the motion of the needle-holding tip. The rate is set slightly above the un-paced heart beat rate.

17 Claims, 8 Drawing Sheets

MOTORIZED MOTION-CANCELING SUTURE TOOL HOLDER

This application claims benefit of provisional appln. No. 60/054,736 Aug. 11, 1997.

This application claims benefit of provisional appln. No. 60/074,656 Feb. 13, 1998.

FIELD OF THE INVENTION

The invention relates to a hand-held suture tool holder for surgery. More specifically, it relates to a holder for the suturing tool (e.g., needle or stapler) moving in synchronization with a surface of a moving organ, such as the heart, so that the surgeon can more easily operate at that surface.

DESCRIPTION OF THE RELATED TECHNOLOGY

In many surgical operations work must be done on a moving organ, such as a beating heart. This requires not only manipulations to perform the operation which would be required in any case (even if the organ were still), but also requires correction of the surgeon's hand motions to compensate for the organ motion so as to keep the surgeon's hands still relative to the work area.

One such operation which has recently been gaining in popularity is known as minimally invasive coronary artery bypass grafting. As described by Calafiore et al., "Minimally Invasive Coronary Artery Bypass Grafting", *Ann. Thorac. Surg.*, 62:1545–1548 (1996), minimally invasive coronary artery bypass (MICAB) is defined as an intervention that does not require median sternotomy or the use of cardiopulmonary bypass (CBP). The incision in the chest wall is small, and the aorta, in any portion, is not the direct source of inflow of blood supply to the bypass grafts. MICAB promises to become an important addition to the surgical treatment of coronary artery disease.

In this technique, the patient is anesthetized and intubated with a single endotracheal tube and hemodynamic monitoring. Short-acting anesthetic agents are used, as extubation of the patient in the operating room is routine. The chest is opened through a fourth or fifth intercostal space incision and the pericardium is opened longitudinally. The left anterior descending coronary artery (LAD) is identified and inspected. The LIMA is harvested through the same incision with or without the aid of a thoracoscope. One or more costal cartilages may be resected to achieve better visualization and dissection of the full length of the LIMA. The artery can be harvested as a pedicle or as a skeletonized vessel.

The patient is heparinized (1 mg/kg), and diluted papaverine is injected into the pedicle and intraluminally into the LIMA through a blunt-tipped cannula. Traction sutures are applied to the edges of the pericardium. After selection of a site for construction of the anastomosis and assessment of the length of the LIMA, distal and proximal control of the LAD is required. A snare of 4/0 PROLENE (Ethicon, Somerville, N.J.) or silicone suture can be applied proximally and distally to the site selected for the anastomosis. Alternatively, the vessel can be opened and a FLOW-RESTER placed intraluminally. The surgical blower (VISU-FLOW, Research Medical, Midvale, Utah) is used for visualization. Electrocardiographic changes, arrhythmias, and ventricular fibrillation are rare events during occlusion of the LAD. Traction sutures can be applied to the visceral pericardium lateral to the LAD, thereby allowing for better stabilization of the artery. Alternatively, a suction device (Medtronic Inc., Minneapolis, Minn.) or a stabilizer (CTS Inc.) can be used. Short-acting β-blockers or calcium channel blockers are used to reduce heart rate when necessary.

The LAD to LIMA anastomosis is performed using a 7/0 or 8/0 running PROLENE suture, either as a single suture or as two strategically placed sutures at the toe and heel of the LIMA. Some surgeons prefer interrupted sutures. At completion of the anastomosis, heparin is reversed with protamine sulfate. Closure of the chest is as in any standard thoracotomy, leaving a pleural tube for drainage. An intrapleural catheter is placed for pain control. The patient is extubated in the operating room or shortly thereafter. Patency of the artery is confirmed by standard Doppler (velocity) echocardiography intraoperatively and by duplex scanning of the LIMA early and late postoperatively in every patient. This is usually done 2 to 3 hours postoperatively and 24 hours after operation. Diastolic flow predominates in a patent LIMA. Most centers report early discharge from hospital and significant cost savings associated with this procedure.

It has been reported that by mid-1996 at least 200 MICAB procedures had been performed in various universities and private hospitals in the United States and several hundred more in Europe and South America (Hartz, "Minimally Invasive Heart Surgery", *Circulation*, 94:2668–2670 (1996)). For other respects about such surgery, see also Calafiore et al., "Left Anterior Descending Coronary Artery Grafting Via a Left Anterior Small Thoracotomy Without Cardiopulmonary Bypass", *Ann. Thorac. Surg.*, 61:1659–1665 (1996); Stanbridge et al., "Minimal-Access Surgery for Coronary Artery Revascularization", *Lancet*, 346:837 (1995); Acuff et al. "Minimally Invasive Coronary Artery Bypass Grafting", *Ann. Thorac. Surg.*, 61:135–137 (1996), and Subramanian et al. "Minimally Invasive Coronary Artery Bypass Surgery: A Multi-Center Report of Preliminary Clinical Experience", *Circulation*, 92 (Suppl. 2):645 (1995).

While such operations have been successfully performed in many different centers, substantial risks are involved in performing surgery on a beating heart. In such operations the arteries are small, the stitches fine, and the sutures are liable to rip due to the heart motion. The risk to the patient is considerable. There have been cases in which the arterial walls were ripped, requiring the operation to be aborted and causing complications.

At first blush it might appear that the heart's motion, being regular, could be easily compensated for by the surgeon. However, the heart motion amplitude is about a half inch (1.3 cm), and this is quite large compared to the precision required of the surgeon's manipulations. The rhythm is erratic. The motion tends to sudden pulsations rather than a smoothly-varying motion such as a sinusoidal motion.

Thus, the acceleration of the heart surface changes rapidly. During the intervals of high acceleration the surgeon is substantially unable to do anything beyond keeping the instruments near their positions relative to the heart, so that no suture rips or unintended punctures occur. The operation is actually performed intermittently during the lulls of low acceleration.

Because of these difficulties, the heart is often artificially slowed down during operations, as discussed above, such as by means of short acting β-blockers or calcium channel blockers. This improves the surgeon's situation in proportion to the change in rate, but for obvious reasons the degree of improvement is limited.

Moreover, the heart (like most organs) responds to stimulation. A suture needle prick often causes this muscular organ to twitch strongly, which is very difficult to compensate for. Twitching will not be lessened by slowing the heart down.

Calafiore et al., supra, report that stabilization of the heart during construction of the anastomosis is an important aspect of the procedure, and devices are being developed that will aid the surgeon during this critical part. However, physically immobilizing the heart is a less than desirable technique as it could damage the heart or impair circulation during this period.

Devices for surgery on a beating heart were reported in a front-page story in the *Wall Street Journal* of Apr. 22, 1997. The story said that CardioThoracic Systems, Inc. is marketing a device resembling a two-pronged fork which is pressed against the beating heart to stabilize the pressed region and allow the surgeon to operate. The cost is $1850 per operation. Another device, sold by Medtronic, is called the "Octopus"; it costs $10,000. Others are expected to be marketed soon by Baxter Inc. and U.S. Surgical Corp.

The CardioThoracic system can only be used in about 20% of all bypass operations, according to the article. Triple and quadruple bypass and valve repairs require stopping the heart.

Pressing on the heart naturally will affect the blood flow through it, and the amount of pressure is limited. The problem of twitching is not overcome, and it appears that the heart surface cannot be immobilized completely.

The new devices "set off intense debate over safety and economics", according to the article. "Some surgeons are particularly skeptical that joining tiny blood vessels on the surface of the heart can be done as successfully while the heart is beating—the CardioThoracic way—as when it is stopped. . . . During a recent [stopped-heart] operation, Dr. Colvin [of New York University Medical Center] peered through magnifying goggles as he performed the delicate task of joining the replacement vessel to a coronary artery, using a tiny needle and barely visible sutures. 'At this point, if you're doing it "beating-heart" you're cursing a mile a minute', he remarked."

The article also reported on a stopped-heart kit which is being aggressively marketed in competition with the CardioThoracic device. Produced by Heartport Inc., it costs $5000 per kit. It has been used in about 500 cases. Like the CardioThoracic method, the Heartport method avoids opening the ribcage, instead using a smaller opening. Because opening the ribcage is a traumatic and painful operation, patients are more likely to chose an operation which requires only a smaller opening.

However, the Heartport method involves stopping the heart with a balloon in the aorta and drugs, and using a heart-lung machine to keep the patient alive during the operation.

The article noted that stopping the heart is stressful and dangerous, and is impossible if the patient is too sick. The cost of using the heart-lung machine is as much as $2,300 (the machines cost about $150,000) and about 6% of patients suffer complications, including stroke, depression, and severe infections. The ideal heart operation would need only a small incision, like the Heartport and CardioThoracic operations; avoid the expense and risk of a heart-lung machine, like the CardioThoracic operation; and stop the heart so the surgeon can safely operate on the delicate arteries, as in the Heartport operation. None of the available operations or devices achieve all these.

The prior art has not solved these problems of working on a moving organ, despite the great need for improvement.

Known hand-held sewing machines cannot provide a solution. One early example is disclosed in U.S. Pat. No. 0,850,779 to Peacock, showing a hand-held awl with a sewing needle automatically moving in and out at the tip of a shank. The needle motion, coaxial with the shank, is adapted to puncturing into a surface perpendicular to the shank and there is no provision for timing the needle motion.

Conventional sewing machines (machines forming stitches) which are miniaturized for hand-held use are known, and are used in the medical area. Skaller, in U.S. Pat. No. 2,580,964, shows a swinging arm 37 with a needle 43 at its tip. The needle 43 moves transversely as the arm oscillates around pivot pin 38. The needle is removably secured to the arm by a screw 44. A bicycle-type sheathed cable is used for actuating the device, with the cable motion being rotary. The arm motion is solely for sewing, and the needle oscillates "in timed relation with the rotation of the looper shaft 28" (column 2, lines 31–34) and their motions are coordinated (lines 42–48).

Conventional technology, as illustrated in these patents, does not provide any apparatus or method for canceling relative motion when an organ such as the heart moves. In the case of a moving organ, such as the beating heart, the surgeon must compensate not only for the motion of the heart but also for the motions of the needle which are completely uncorrelated to the organ motion. Apparently hand-held sewing machines, or devices with moving needles or other suturing tools, have never been used to operate on a beating heart, and the reason is probably the near impossibility of compensating for two motions at once.

Co-pending application No. 60/047,349 of the present invention describes a hand-supporting platform which cancels relative motion, for use primarily in MICAB heart surgery. The entire contents of this application are entirely incorporated herein by reference.

In the invention described in said co-pending application, the platform is driven by a specially-shaped cam to move up and down in synchronization with the surface of the heart (or other organ or part). The heart's motion is effectively canceled relative to the platform. The surgeon's fore-arm rests on the moving platform but the operating hand must dangle at least in part over the end of the platform in order that the surgeon may work.

The platform oscillation is matched to the heart surface in oscillation profile, amplitude, and phase. However, the heart surface also has a displacement direction (generally, perpendicular to the heart surface) which is approximated as a straight-line motion in the related application; the platform has a motion which is approximately linear. The motion vector of the platform must be aligned with the motion of the heart, or the surgeon's hand will be jiggled side-to-side, relative to the heart, during the operation. A laser may be used to align the platform, which is supported on an adjustable multi-angle base support attached to a base of the platform. The base angle, and thus the platform motion angle, are adjusted prior to operation. Then the base support, which resembles the adjustable head of a photographic tripod, is locked into position.

This related invention is valuable and is expected to save many lives, but it has certain limitations which are overcome in the present invention. One limitation is that only the anterior surface of the heart is readily operated on because the lateral surfaces are buried deeply in the chest and when the platform is angled over far enough to align the platform motion vector with the heart surface motion vector, the other organs are in between the heart and the platform. Thus, for example, a quadruple bypass operation could not easily be performed with the motion-canceling platform.

Another limitation is that the platform motion is essentially linear. (To be precise, it is an arc of large radius; but with the small amplitude of heart beats the chord is negligible.) The heart surface motion is close to a straight line, but it is of course not exactly a straight line (or for that matter a circle of large radius). Therefore the needle, held stationary relative to the platform by the surgeon's hand, deviates laterally from the heart even when the platform and heart motions are otherwise precisely matched. If the lateral heart motion is roughly circular, a closer match might be made with the platform; but rotating the platform is impractical because of the way it is supported, so the lateral deviation may be in the wrong lateral direction.

SUMMARY OF THE INVENTION

Accordingly, the present invention has an object, among others, to overcome deficiencies in the prior art such as noted above.

The invention relates to a needle holder which overcomes the problems of conventional devices and methods by providing a suturing tool holder, with a handle, that is easily rotated to any angle; and an oscillating needle holder attached to the handle portion. This permits the needle oscillations to be rapidly and easily adjusted for direction, and to be disposed at any angle because the needle-holding portion is small. In addition, the motion of the needle or stapler can be accurately matched to the motion of the heart, both longitudinally and laterally; the heart motion is mimicked.

The heart's motion is thus effectively canceled and delicate operations can be performed with much more ease, and much less risk, than formerly.

In the needle-suturing embodiment the holder of the present invention preferably includes a hooked barrel and a pressing rod for grasping the needle. The rod is pressed against the hook of the barrel through a flexible cable, similar to a bicycle brake cable, which is remotely operable by a mechanism controlled by a pedal or a microswitch on the handle.

A second flexible cable is used to oscillate the entire needle holder within the handle, so that the tip, holding the needle or stapler, moves for operating on the heart. The second cable sheath is fastened to the inside of the handle; at the other end the cable is driven relative to the sheath by a suitable apparatus, preferably including a specially-shaped systole/diastole cam, a mechanism for varying the amplitude to match that of the particular heart surface being worked on, and a trigger switch for driving a heart pacer. Pacing the heart is an important feature of the present invention. A clutch or solenoid may be used for starting and stopping the oscillation by disengaging the cable from the driver.

As noted, the suture tool holder of the invention can be manipulated to any angle and therefore it can be used on the sides of the heart, not only on the anterior surface. Because different areas of the heart have different motions, the cams of this invention should be interchangeable so that different heart motion cam profiles can be used.

Alternatively, a single cam with selectable regions can be used; a quadruple bypass operation would require a four-region cam. Sub-regions could also be provided with different shapes for different body types.

To prevent rotation of the needle holder relative to the handle, a portion of the holder is of non-circular, preferably square, cross section and slides in a similarly shaped opening inside the handle. The non-circular cross section portion of the needle holder is axially straight.

To provide lateral motion adjustment (because the motion of the heart surface is not exactly linear) an arcuate portion of the needle holder slides through a second hole or orifice as the needle holder oscillates to and fro. Since the needle holder is also held by the straight square portion within the square hole, the motion of the arcuate portion through the orifice causes a lateral excursion of the tip.

The tip motion can be adjusted precisely to the motion of the heart surface by aligning the angle and the position of the handle, adjusting the oscillation amplitude, selecting the proper cam, and rotating the handle so that the lateral excursion of the tip is aligned with the excursion of the heart surface.

Rather than driving the tool holder according to the heart's motion, which would require complex electronics, sensors, and servo-motors, the present invention preferably drives the heart according to the predetermined motion of the needle or stapler. The heart is paced by electric signals timed to the oscillations of the tool holder, as detected by a simple momentary-contact switch which is closed once in each oscillation. The switch may be closed by a cam on the cable-driving mechanism which oscillates the needle holder or stapler. Switch closure (or opening) generates a trigger pulse to conventional pacer circuitry, which may provide for an adjustable delay between the trigger pulse and the heart stimulus. Electronic and/or mechanical means to adjustably advance or retard the pacing signal can be used.

The paced heart rate avoids any twitchiness in the heart muscle, which might otherwise cause it to move unexpectedly when touched or pricked. The heart is preferably triggered at a rate slightly above the heart rate to which the heart has been slowed to naturally beat without pacing. It has been found that when the heart is driven at a slightly higher rate, twitchiness is eliminated. Because the present invention is able to easily compensate for heart motion regardless of the beating rate, the operation becomes easier when the heart is paced to beat faster than would otherwise be the case.

Pacing the heart also improves the regularity of the beats and stabilizes the heart oscillation amplitude, because blood flows into the heart chambers at a constant rate and if the filling time for any two beats is identical, then so will the amounts of blood pumped on those beats be identical, and hence also the amplitudes.

Because the heart's motion is non-sinusoidal (as noted above), the present invention uses a rotary cam, driven by an ordinary electric motor, oscillating the tool holder drive mechanism full systole to full diastole. The cam profile is adjusted to match the heart's surface motion. In a preferred embodiment, the drive mechanism includes a platform hinged to a base and the cam position is adjustable relative the hinge position to adjust the amplitude of the platform motion for different sizes of heart. The cam may be interchangeable for different profiles, if needed.

The lobed cam may be replaced by an equivalent of more general motion capability, such as an electrically-controlled actuator driven according to a voltage, digital signals, or the like, and having a pattern that is adaptable to different heart motion amplitudes, phases, or patterns.

To adjust the excursion (oscillation amplitude) and optionally also the synchronization (pacer timing advance or retard), the present invention may employ another simple but effective innovation. Thus, a capacitor may be formed between the heart and the tool holder, and the capacitance of this capacitor will vary with the distance to the heart surface. An electrical oscillating circuit is arranged to use the capacitor as part of an LC circuit resonating in the audible range (or at a frequency that can be sub-divided to reach the audible range). Using conventional circuitry, power supply, and loudspeaker or earphone, the invention can provide an audible tone whose frequency is very nearly proportional to the heart-holder distance.

It is well-known that the ear can hear very slight frequency changes, and because of this a surgeon listening to the tone generated in the heart-holder capacitor circuit will be aware of distance variations of less than one percent. Adjacent keys on the piano differ by six percent. The surgeon can then adjust the drive and/or the pacer electronics to minimize the frequency variation of the audible tone. When the motion is completely synchronized with the heart, then the tone will be flat, of constant pitch.

The oscillation is thus matched to the heart surface in oscillation profile, amplitude, and phase, which is a complete specification of the vibratory motion. To align the motion vectorially to the heart, the surgeon merely adjusts the angle with his or her wrist and/or rotates the handle.

The present invention solves a life-threatening problem which has not been even partially solved before (except by the Applicant's related platform invention) by eliminating relative motion between a moving organ and a surgeon's hand. The extreme simplicity of the invention is facilitated by the innovation of driving the heart to follow a mechanical oscillation. The consequent reliability, ease of use, and low cost and reliability are very unusual in the medical field and are great advantages. The present invention permits operating on areas of the heart other than the anterior surface that is accessible to the motion-canceling platform.

BRIEF DESCRIPTION OF THE DRAWINGS

The above and other objects and the nature and advantages of the present invention will become more apparent from the following detailed description of preferred embodiments taken in conjunction with drawings, wherein.

DETAILED DESCRIPTION OF THE PREFERRED EMBODIMENT

Here, and in the following claims:

"Synchrony", "synchronously", and related forms of this word mean at the same frequency, but not necessarily at the same amplitude, pattern, or phase.

"Pattern" of an oscillation relates to the repeating shape of a graph of the oscillation as plotted against time. For example, if the displacement (in inches or centimeters) in a certain direction of one portion of the surface of a beating heart were to be graphed as a function of time, the graph over the period of one beat would be a pattern. Graphs could also be made of heart surface velocity or acceleration, and these also would represent patterns.

"Vector" in reference to heart oscillation (or a matching oscillation) means a line drawn between the position of a point on the heart surface at full diastole and the position of the same point at full systole.

Figure 1:
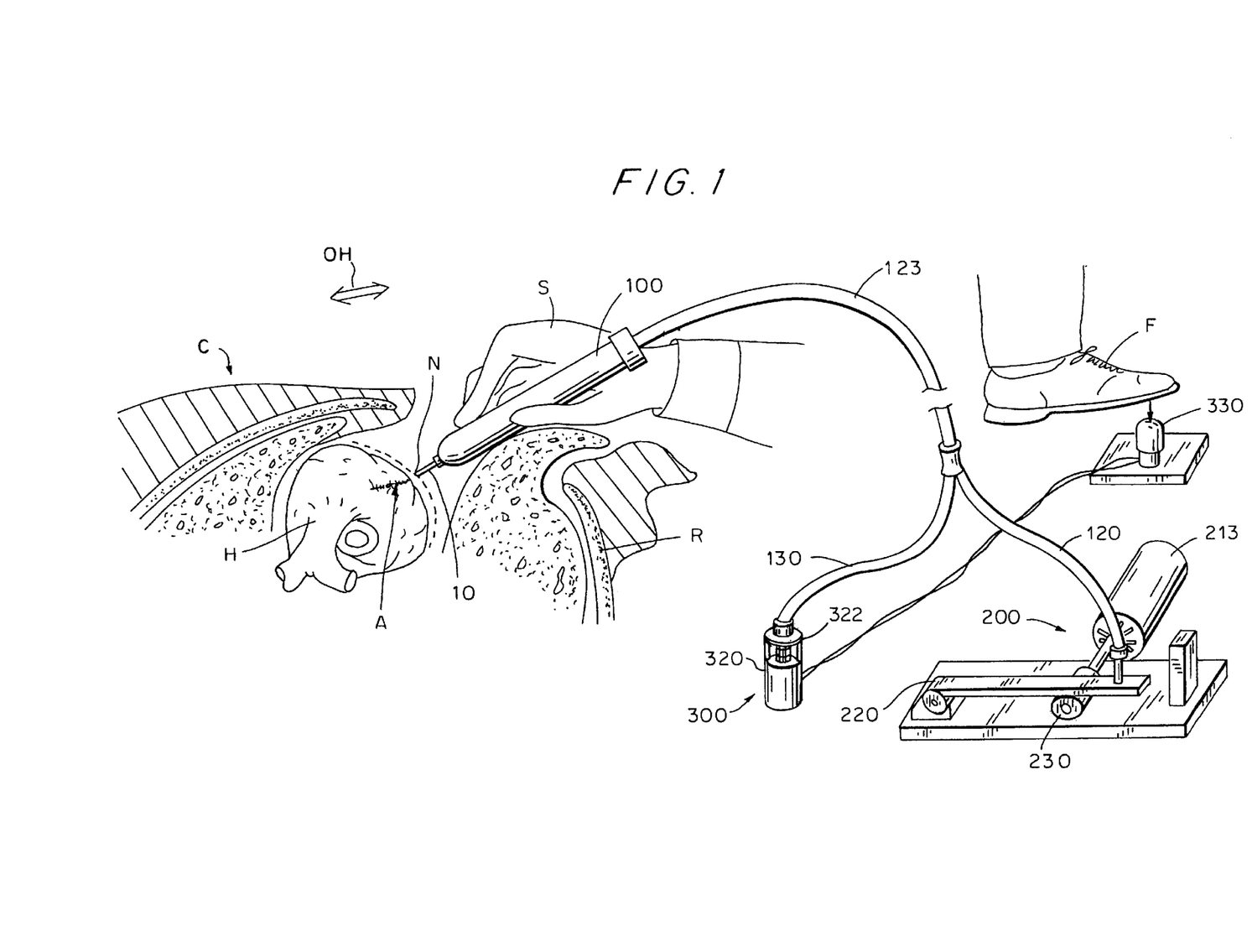
FIG. 1 is a partly schematic, partly perspective, and partly cross-sectional view of the apparatus of the present invention while in use.

FIG. 1 shows the present invention in relation to a patient's chest C and heart H, which is being operated on by the hand of a surgeon S holding a handle 100 of the motion-canceling present invention. A coronary artery A, which is the site of an anastomosis, is shown on the surface of the heart H. The chest C is shown in cross section, but the heart H, handle 100, and surgeon S are not. A rib R is partially removed.

The heart H is beating during the operation and its surface, with the artery A, is moving up and down in a heart oscillation which has a certain motion pattern (wave-form), amplitude (displacement over one beat cycle), and frequency (beating rate). The heart oscillation is indicated in FIG. 1 by an arrow labeled OH, which is offset from the artery A, the motion of which it describes, for clarity.

The invention includes a driving mechanism 200 which moves up and down in an oscillation which mimics the heart oscillation OH in pattern, amplitude, and frequency. Because the oscillation follows the heart oscillation OH, the surgeon S can easily operate on the moving heart. The oscillation mechanism is adapted to cancel the relative motion between the surgeon S and any particular place on the heart H, whose surface motion varies with surface location.

At the tip 10 of the handle 100 is a suturing needle N which is used for anastomosis of the artery A. While the hand of the surgeon S remains stationary, the needle N oscillates in coordination with the artery A, so that the surgeon S need not compensate for the motion of the heart H. While the preferred embodiment is illustrated in which the tool in a suturing needle, it should be understood that the present invention comprehends the use of other tools for suturing, such as staplers, lasers, adhesive applicators, and so on; the present invention further comprehends the use of non-suturing surgical tools, such as a scalpel, for any other sort of task to be performed on a moving organ.

The tip 10 of the handle 100 is coupled to a tool-drive mechanism 200 and to a tool-grip mechanism 300, preferably via a compound bicycle-type cable 123 which contains two distinct cables 120 and 130, into which it preferably splits once away from the operating area. The bicycle-type coaxial cables include a sheath that is flexible but resistant to kinking and collapse, and an internally movable element, such as wire rope, which can transmit push-pull forces and/or rotational forces along its length when held within the sheath. The invention can equally well use hydraulic, pneumatic, electric, electronic, or other conventional actuators in place of the bicycle cables.

The tool-grip mechanism 300 causes the tip 10 to grip and release the needle N. It includes a solenoid 320 adapted to pull on the central wire of the cable 130, to release the needle N as explained below, whenever the surgeon's foot F steps on a foot switch 330, wired to the solenoid 320. (The necessary electric power source is not shown in FIG. 1, but this is strictly conventional). A return spring 322 is rigged to push the central wire into the sheath of the cable 130, causing the tip 10 to grip the needle N.

The whole mechanism 300 constitutes a means for releasing the needle N when the switch 330 is depressed, and gripping the needle N at other times. In alternative embodiments gripping, rather than release, could be the passive or non-activated action.

Figure 2:
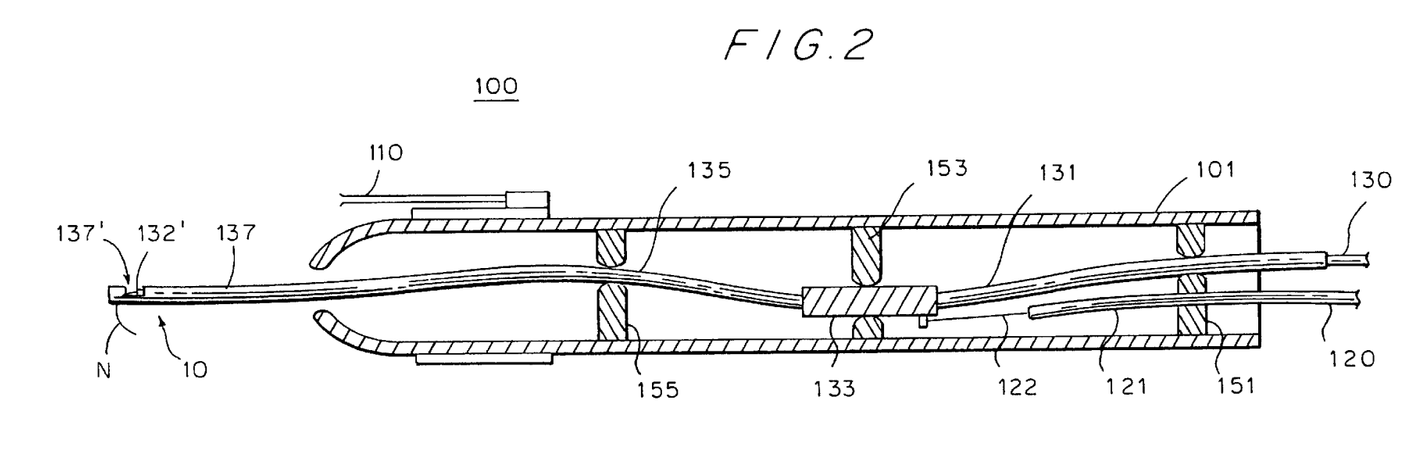
FIG. 2 is a cross-sectional view of the handle.

An alternative to the foot switch F, a finger-activated microswitch 110 on the handle 100, is shown in FIG. 2. Any other sort of control, including voice control, is within the scope of the invention.

In an alternative embodiment gripping and release of the needle N, or a stapling operation, might be actuated by a two-portion slidable handle in which a palm portion and a sliding finger portion are relatively moved, by finger motions, to grasp a needle (or close a staple). This embodiment is not illustrated in the drawing, but is related to the Applicant's co-pending application entitled "Coaxial Needle Holder", serial number not yet assigned, the contents of which are entirely incorporated herein by reference.

FIG. 2 shows the inside of the handle 100, including a handle housing 101 into which the cables 120 and 130 couple at the right side of the drawing and from which the tip 10 emerges at left. The outer sheath 121 of cable 120 is fastened to the handle at end stop 151 of the handle 100, so that sheath 121 cannot slide through the end stop 151. On the other hand, the sheath 131 of cable 130 is free to slide through the end stop 151.

The wire 122 of cable 120 extends to a carrier 133 which is fastened to the outer sheath 131 of cable 130. Carrier 133 is axially forced to and fro by the wire 122 and slides within the middle stop 153. This moves the carrier 133 and the tubular sections 135 and 137, which continue the bore of the sheath 131 but are preferably rigid.

The inner wire continues through the bore from cable 130 to the tip 10, where it terminates in a rigid portion 132'. The rigid portion may be formed, for example, by soldering the end of the wire 132 or by fastening a solid tip portion onto the wire. The rigid portion 132' protrudes into a transverse slot 137' at the end of the tube portion 137, which is closed at the very tip end, so that the needle N may be inserted and held when the rigid portion 132' presses the needle N against the side of the slot 137' farthest from the handle housing 101. This gripping action is controlled through the mechanism 300, as discussed further elsewhere.

The illustrated structure allows the entire tip assembly (tip 10 with slot 137', tube portion 137, tube portion 135, carrier 133, and cable sheath 131), pushed by wire 122, to slide so that the tip 10 moves in a generally axial direction for motion cancellation; the needle N is able to be grasped and released independently of the cancellation motion. Thus, the surgeon can grasp and release the needle N at will, using cable 130, while the tip 10 is moved by cable 120 so as to cancel all relative motion and effectively "stop" the heart.

Preferably both the carrier 133 and the hole in the middle stop 153 are square (or otherwise non-circular) in cross section so that the carrier 133 cannot rotate about the axis of the handle 100. The fit is close, and this locates the transverse position of the carrier 133 at the middle stop 155. The carrier 133 extends into a tube 135 which is bent into a particular shape. This shape is adapted to refine the lateral motion of the tip 10, as follows:

The tube 135 passes, in a close-fitting but freely movable manner, through a hole in a front stop 155 which is fixed to the handle 100. This hole, along with the square hole in the middle stop 153, fixes the orientation of the relatively rigid tip assembly comprising the tube 135 and the carrier 133. Because the tube 135 is (preferably) curved, the tip 10 moves laterally as the tip assembly slides axially through the two holes in stops 153 and 155. The lateral motion of the tip 10, at the end of tube 137 (which is merely the continuation of tube 135) is amplified due to the length of tube 137. The hole in middle stop 155 is optionally offset from the center line of the housing 101 as shown.

This structure adapts the motion of the tip 10 to any heart surface motion, not just a straight-line motion. This is useful because the heart is not a simple object like a balloon, expanding and contracting in a simple way: it is complex in structure and also in motion. A point on the surface of the heat, such an anastomosis site, may not move radially inward and outward in a straight line; it might instead move generally in and out, but with a lateral digression, in a curve.

If the tube 135 is perfectly straight, and also parallel to a line joining the centers of the two holes through stops 153 and 155, then the tip 10 will oscillate in a straight line, and will follow the heart surface if it moves along a straight vector.

If on the other hand the tube 135 is not straight but curved, then the tip 10 will follow a curved path, with a lateral deviation from a straight line. Any desired deviation motion can be easily be achieved by choosing the appropriate curve for the tube 135 where it passes through the middle stop 153; and the motion of the tip 10 can be made to follow any heart surface motion with any curvature at all.

Moreover, the curvilinear motion can be adjusted by moving the stop 155 along the inside of the housing 101. As the stop engages different portions of the curve of the tube 135 the shape varies and so does the tip 10 motion.

The present invention comprehends each of centered stop holes, straight tube portions, and straight vector tip motions as particular cases of the lateral-deviation structures for general curved motions of the tip 10.

In use the handle 100 is rotated about its longitudinal axis to bring the lateral deviation of the needle N in line with the lateral deviation of the heart H. That is, once the handle 100 is aligned with the vector of the heart motion, i.e. is parallel to the straight line connecting the inmost stopping point and the outermost stopping point, then the lateral deviation of curved motion of the tip is likely to be in the wrong direction. When the handle 100 is rotated about its longitudinal axis, the deviation of the tip 10 and the deviation of the heart can be aligned. The handle 100 is preferably cylindrical for this reason. However, the present invention comprehends handles of other shapes such as pistol-grip, curved, T-shaped, and so on.

Alternatively, the front stop 155 can be eliminated in favor of the constriction at the front end of the handle 100, which in the illustrated embodiment is large enough to freely pass the tube 137 without contact but which may be made the same size as the hole in stop 155, i.e., slightly larger than the outer diameter of tube 137. The tube portion labeled 137 would then be curved to produce the desired motion of the tip 10 and the needle N.

The housing 101 is preferably of metal or engineering plastic material, and may be made in two halves for easy cleaning and sterilization. The tube portions 135 and 137 are preferably of stainless steel or other strong, sterilizable material. The stops 153 and 155, on which the tubes 135 and 137 rub, may be of low-friction material such as nylon to avoid any need for lubrication. The bicycle type-cables 120 and 130 are preferably made with materials adapted to easy disassembly and sterilization as well as to low friction. They may include low-friction sheaths to avoid lubricants.

Figure 3:
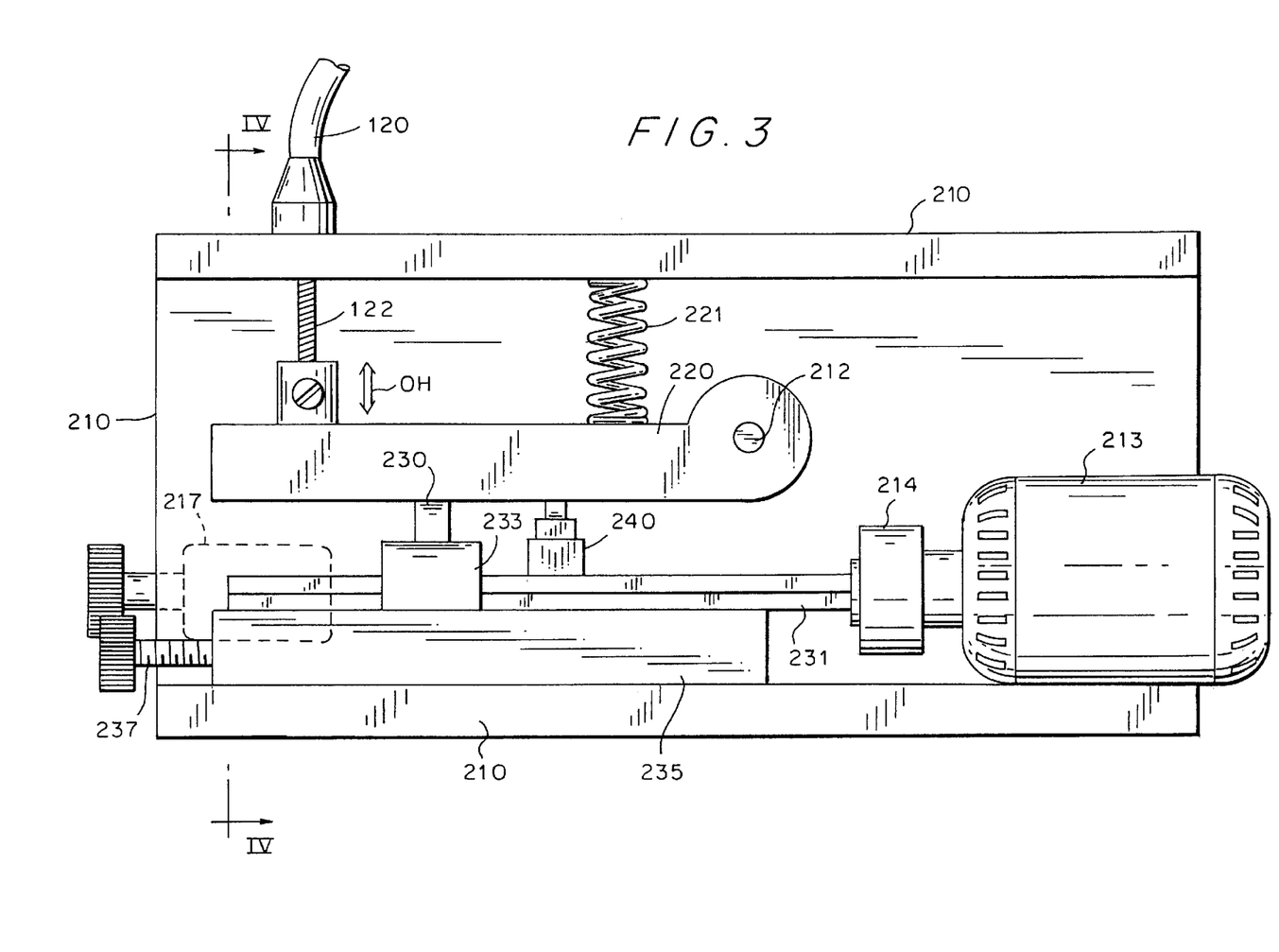
FIG. 3 is an elevational view of an oscillation mechanism.
Figure 4:
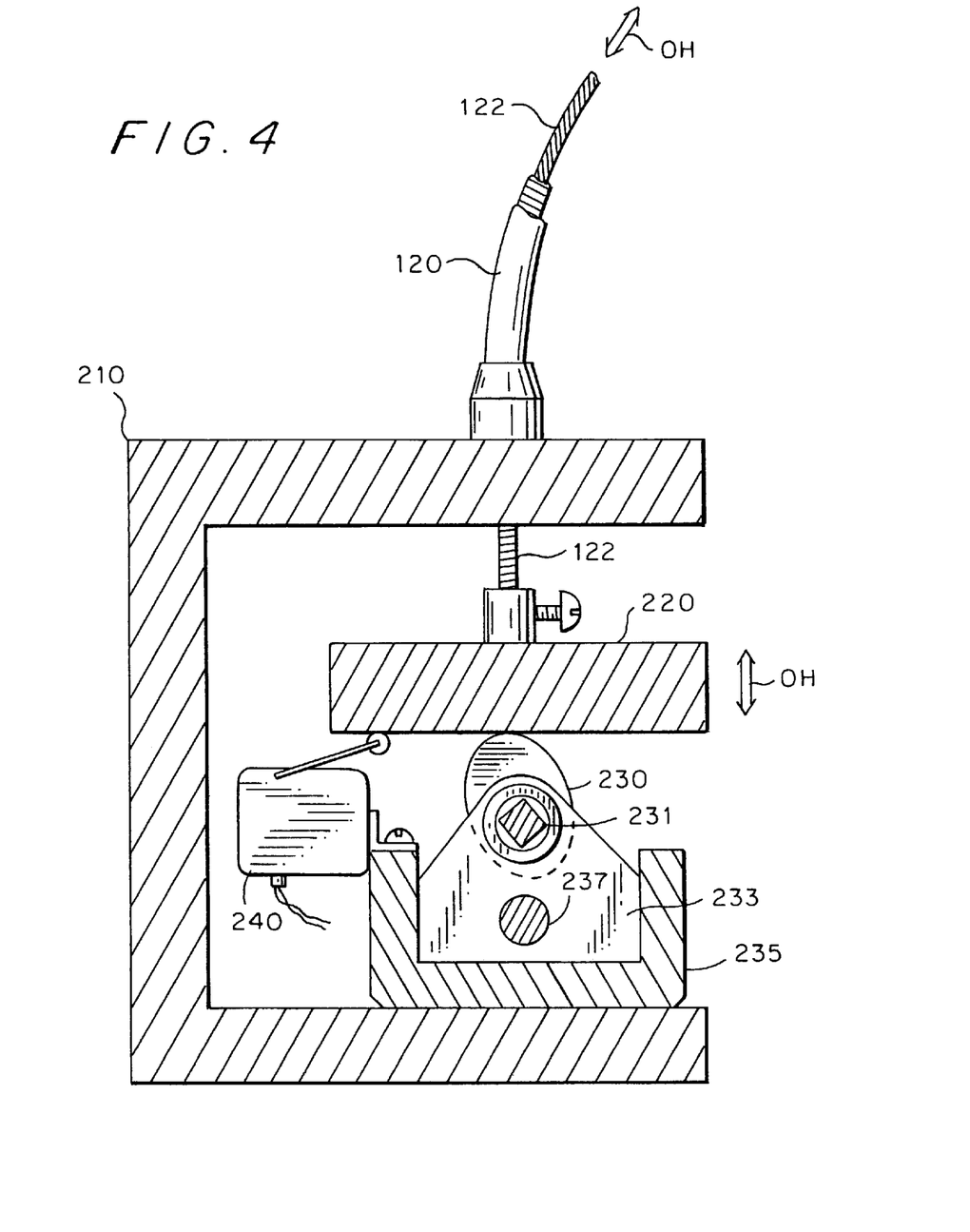
FIG. 4 is a cross section on lines IV—IV of FIG. 3.

FIGS. 3 and 4 show, in greater detail, an embodiment of tool-drive mechanism 200 which causes the tip 10 and the needle N to oscillate for motion cancellation.

An arm 220 is hinged at one end to a base 210 by a hinge 212 and is driven into oscillation (indicated by arrow OH) by a rotating cam 230 which bears against the underside of the arm 220. The cam 30 is slidably but non-rotatably mounted on a cam shaft 231 which is rotated by a motor 213. The motor 213 is mounted to the base 210 and is coupled to power and control circuitry (not shown in FIGS. 3 and 4). The cam 230 profile is chosen so that the oscillation OH has the correct wave-form or temporal pattern of displacement, velocity, and acceleration (which is generally not a simple sinusoidal shape, although that is within the scope of the invention).

The cam 230 bears against the underside of the arm 220 and pushes the arm 220 up and lets it fall down, so that the cam 230 and the arm 220 stay in contact. A push-down return spring 221 is shown in FIG. 3. Dual opposed counteracting actuators (or a double-acting single actuator), not shown, may be used in the invention as an alternative to the cam mechanism.

The cam 230 may be molded of a strong, low-friction material such as nylon. The profile of the cam 230, which creates the pattern of oscillation OH to match that of the heart, is visible in FIG. 4. The cam surface appears as a curved line; this shape embodies the profile.

The cam 230 is driven by a cam shaft 231 which may be of square section to engage a square hole in the cam 230 (not visible in FIG. 4). The shaft 231 is supported in bearings in a slider 233, which moves in a channel 235 rigidly attached to the base 210. The amplitude of oscillation is adjusted by moving the slider along the channel (in and out of the plane of the paper in FIG. 4, left-to-right in FIG. 3) by means of a threaded rod 237 which engages a threaded hole in the slider 233. The threaded rod 237 is preferably driven by a motor 217 mounted to the base 210 (shown by dashed lines FIG. 3, as it is behind the vertical wall of the base 210).

Thus, the motor 213 turns the cam shaft 231, which rotates the cam 230, which drives the arm 220, which is coupled to the wire 122 of the cable 120 which drives the tip 10 of the handle 100 in the heart-pattern oscillation OH. The motor 213 is preferably continuously powered and the oscillation OH controlled by a clutch 214 disposed between the motor 213 and the cam shaft arm 231. When the clutch 214 is disengaged the cam shaft 231 does not rotate, and neither the cable 122 nor the tip 10 (FIG. 1) oscillate with the motion OH. The clutch 214 may be engaged and disengaged in any conventional manner using pedals, triggers, switches, etc.

Because the present invention permits operations on various widely-separated areas of the heart, with various patterns of surface oscillation OH, different cam profiles may be needed. Accordingly, the cam 230 may be interchangeable with other cams and/or alternatively may include a variety of different shapes which may be chosen for different heart areas and different patients, as the heart oscillation pattern varies with body type.

Figure 5:
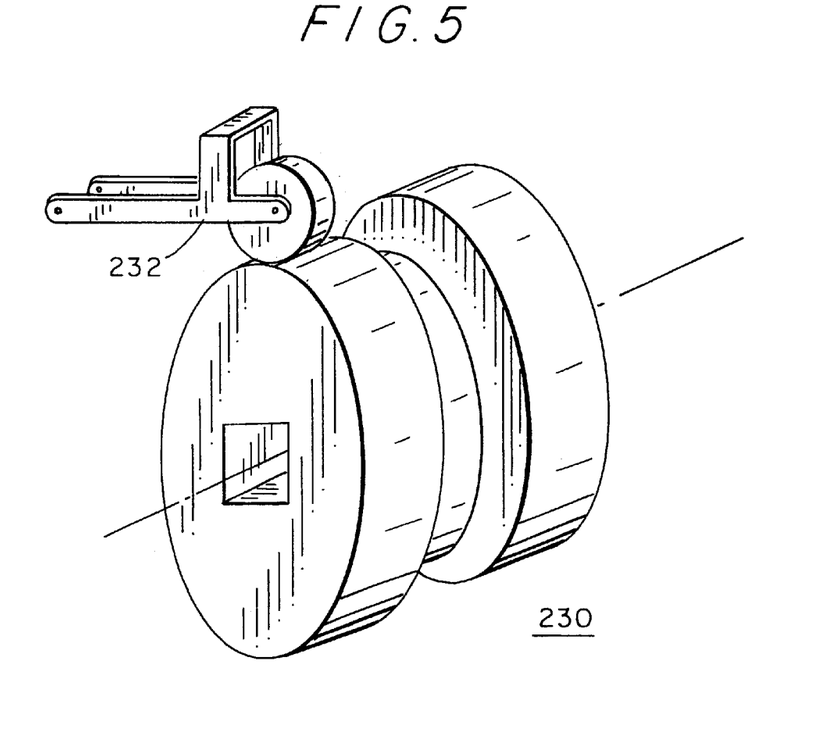
FIG. 5 is a perspective view of a multi-lobe cam.

FIG. 5 shows a cam 230 with different sections having different profiles. There is no need to vary the radius, because the oscillation amplitude is adjusted by the varying the distance of the cam 230 from the hinge 212 with the motor 217; or the phase, since that can be set in the pacing circuitry (described below). Only the shape needs to change. To selectively engage just one profile of the cam 230, a tappet 232 or some other conventional device can be used. The cam 230 of FIG. 5 may be molded in one piece or machined from a single block of material.

In order to virtually cancel the organ motion the oscillation OH of the needle-holding tip 10 should match as precisely as possible the motion of the artery A being operated on in phase, amplitude, frequency, and pattern. As noted above, the tool-drive mechanism 200 permits adjustment of the pattern by cam profile selection, and the amplitude by cam-hinge distance. The frequency is determined by the rpm's of the motor 213. The phase is preferably adjusted electronically as discussed below.

A momentary-contact switch 240 is mounted on the channel 235. The switch 240 provides a trigger signal to a pacer (not shown in FIGS. 3 and 4) which drives the heart to beat at a rate preferably slightly higher than its rate when not paced. The switch 240 could also be mounted on the slider 233 or be incorporated into the base 210, for example in a triggering cam coupled to the driven end of the cam shaft 231. Any conventional trigger means is comprehended by the present invention, including magnetic and optical triggers or triggers coupled to the drive circuits of the motor 213.

Figure 6:
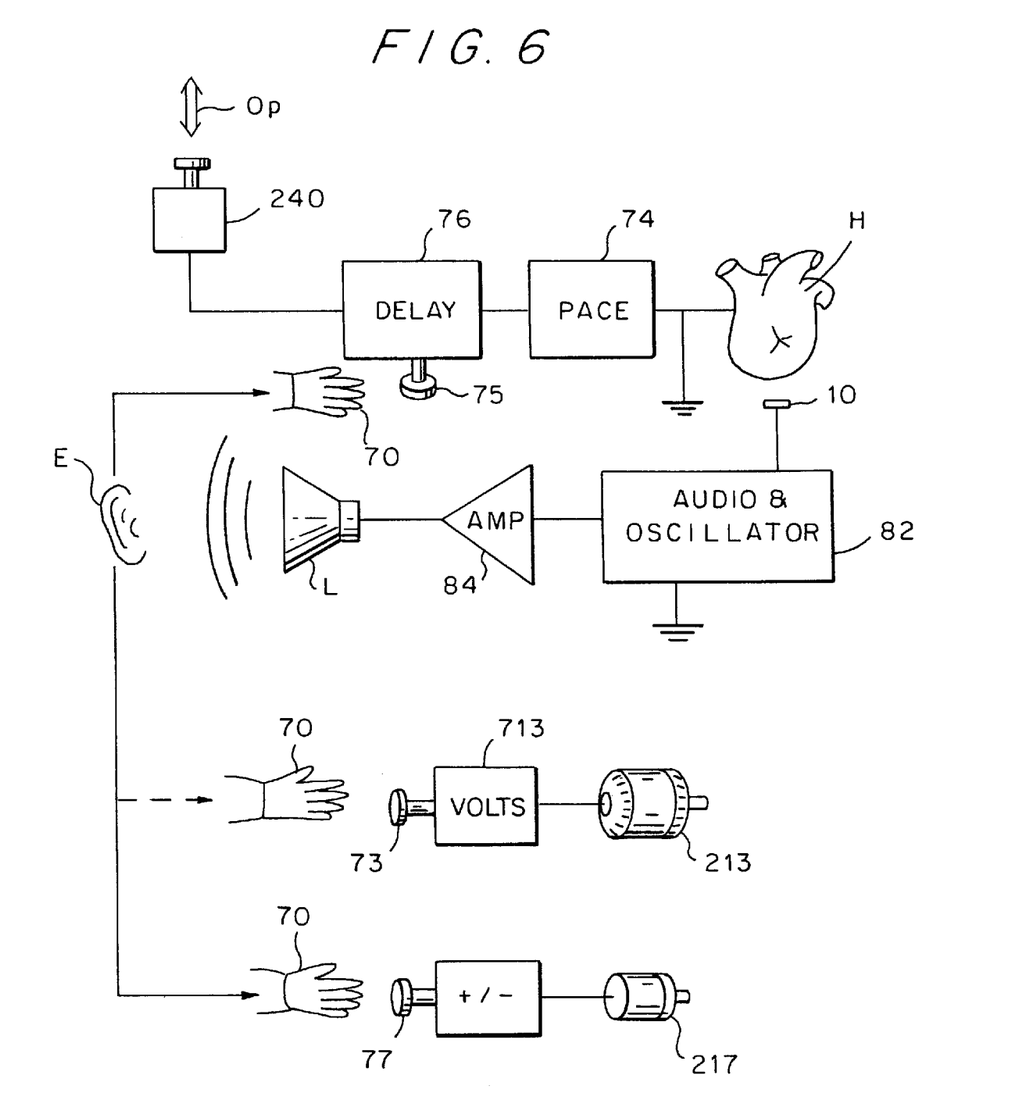
FIG. 6 is a schematic view of motion control.

FIG. 6 illustrates the control of these parameters. The surgeon first notes the heart rate without any pacing stimulus, preferably after slowing the heart beat by means of short acting β-blockers or calcium channel blockers, and then adjusts a voltage supply 713 driving the motor 213 to set the oscillation rate slightly higher than that rate. Motor 213 may be a DC motor speed-responsive to applied voltage, or some other type with appropriate speed-control circuitry 713. The adjustment is illustrated schematically by a hand 70 and a knob 73. The pace circuitry is powered, and the heart H is now driven to beat at an elevated rate, which not only makes its beating much more regular (i.e., at a precise frequency) but also prevents "twitchy" reactions by the heart muscle, which could cause an error in the operation.

Pacing results from the oscillation of the arm 220 activating the switch 240, which sends a trigger signal to the pace circuit 74, which stimulates the heart H once for each trigger signal, i.e., at the frequency of switch triggering. The invention optionally includes an adjustable delay circuit 76 between the switch 40 and pace circuit, as illustrated schematically by the hand 70 and a knob 75 on the delay box 76. The delay adjust may be either mechanical or electronic.

Optionally, the needle-holding tip 10, which forms a capacitor with the heart surface, may be used to monitor the distance between the heart and the tip 10. The heart H preferably is grounded either through the chest C and patient supports or by an electrode (not shown). The capacitance value of the capacitor formed by the heart H and tip 10 is a function of the distance between them.

FIG. 6 shows an audio oscillator 82, such as a grid-dip oscillator, used to generate a frequency that is a function of the capacitance; this frequency is amplified by an amplifier 84 and turned into an audible tone by a transducer L (loudspeaker, earphone, etc.); the tone is heard by the ear E of the surgeon. The surgeon can detect any mis-match between the oscillation OH and the heart motion by listening to the tone, because when the oscillations are different the distance will vary and the tone will warble. This provides feedback on the synchronization, phase locking, and amplitude differences of the oscillation OP and the heart oscillation OH.

A difference in amplitude will cause a regular pitch variation at the common frequency of the heart and tip 10. The surgeon adjusts the position of the slider 233 (FIGS. 3 and 4) by driving the motor 217 one way or the other, to turn the threaded rod 237 clockwise or counter-clockwise until the tone variation is minimized, as illustrated by hand 70 and control knob 77. Then the surgeon might also adjust the phase with the pacing trigger delay 76 to further reduce warble.

If the tone changes slowly over a number of beats, this indicates that the heart H is not following the pacer or the pacer is not following the trigger signals.

The tone also provides feedback about the shape of the cam, since if the profile is not correct then warble will be heard (even if there is no mis-match in frequency, phase, or amplitude) because of differences in the oscillation patterns. If the profile is adjustable, then the surgeon can adjust this as well.

All the above steps can be done with the handle 100 rigged near the heart in a clamp or holder (not shown) so that the surgeon may attend to the adjustments with both hands and without having to hold one hand stationary. When the tone variation is stable and adjusted to minimum variation, then the surgeon is ready to operate.

When the needle N is grasped in the slot 137' the capacitance between the tip 10 and the heart H will of course be much different than when the tip 10 is empty. This will cause a large shift in the frequency of the grid-dip output signal. However, such shifts, and also those resulting from the movements of the surgeon's hand (S, FIG. 1) will not hinder the operation because the tone will change only in response to the surgeon's voluntary motions: these tone changes will actually provide feedback to the surgeon, and the superimposed warbling due to imperfections in the oscillation OH of the tip 10 will still be audible.

Figure 7:
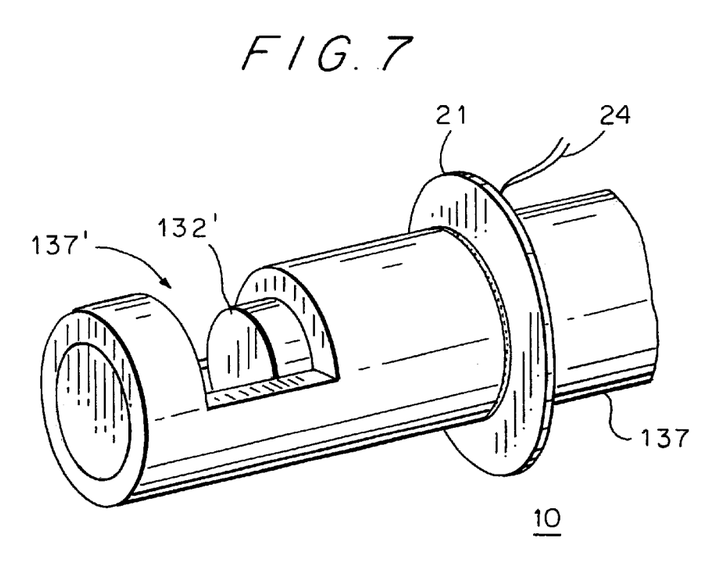
FIG. 7 is a perspective view of a tip with an auxiliary annular capacitor plate.

FIG. 7 shows a possible solution to the problem of the tone disappearing when the tip 10 or needle N touches the heart H, shorting out the capacitance. An insulated capacitor plate 21 is fixed on the tube 137 but is insulated from it and independently connected electrically to the oscillator 82. The plate 21 is coupled to a capacitor wire 24, which may include a grounded shield (not shown).

Optionally, a laser of the ordinary laser pointer type (not shown) can be used to help in aligning the handle 100. The laser can be held in the suturing hand and the laser beam directed along the vector of the heart oscillation. The surgeon can watch the motion of the beam on the heart surface. When the heart surface is moving perpendicular to the beam, the lateral location of the laser spot on the heart will be stationary, even though the beam spot moves in and out along the beam line. The displacement of the beam spot along the heart surface while the heart is beating will be zero. Conversely, if the heart surface is moving at an angle to the beam, the beam spot will traverse laterally across the surface, regardless of the angle which the heart surface makes with the beam. The sideways beam displacement will be readily apparent to the surgeon, and the angle can easily be adjusted to align the laser.

Then, the laser can be replaced with the handle 100. If the two implements are the same size, the handle 100 will be pre-aligned once it is grasped. Alternatively, the handle 100 can be adapted to emit a laser beam axially, which avoids the need for changing implements while holding the hand stationary.

The invention comprehends variations on the preferred embodiment described above.

The present invention allows a surgeon or veterinarian to operate on any moving organ, and the operation is not limited to the surface. The invention permits canceling of relative motion between a tool holder and an exterior or interior portion of a beating heart or any other organ. A surface is, of course, only one particular type of portion of an organ.

The adjustments which the surgeon makes to the oscillation phase and amplitude can also be made by automatic equipment. The invention also comprehends means for manually or automatically augmenting the cam motion or modifying the cam profile.

The capacitive plate 21 can be projected outward and down from the end of the tip 10 to be adjacent the portion of the heart H that is to be operated on. In one embodiment, a pattern-remembering computer can be a coupled to the capacitance probe circuit which will "learn" the deviations between the heart and tip 10 that recur in every cycle and anticipate them; this will result in greater accuracy. Known sonar or radar distance measuring techniques may be used as alternative to capacitance.

Figure 8:
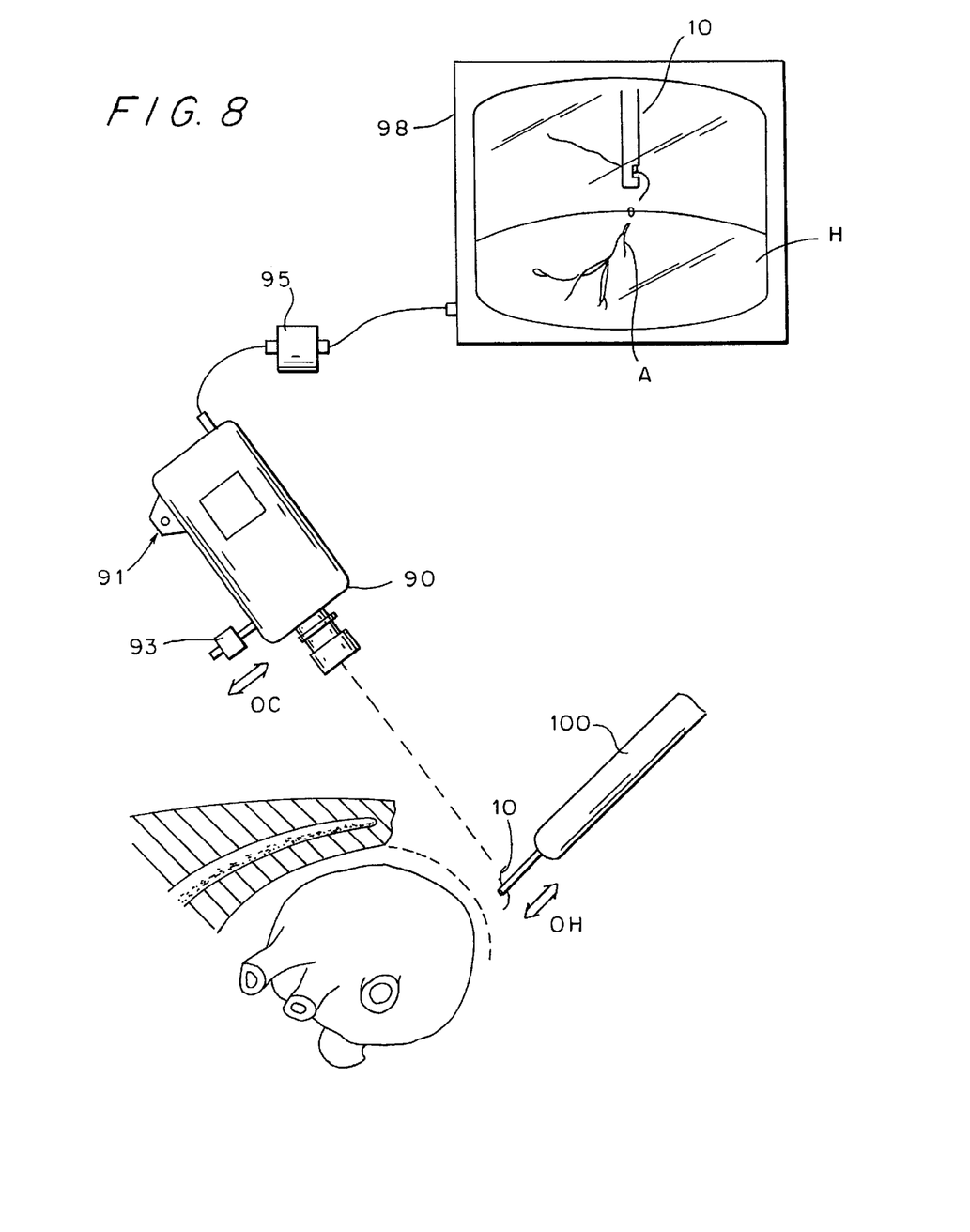
FIG. 8 is a schematic view of motion-canceling TV imaging.

FIG. 8 shows an embodiment of the invention in which TV imaging is included. Preferably, the TV image is stabilized so that the surgeon or a technician or nurse can watch the operation as if the heart were still. The same motion-canceling principle is applied to the TV image.

A TV imaging camera 90 is shown in FIG. 8 trained onto the operation; the TV image is displayed on a monitor 98. To immobilize the image on the monitor 98, the camera 90 may be swung mechanically on a pivot 91 by a camera actuator 93 driven in an oscillation OC by a third bicycle-type cable from the mechanism 200 (not shown) or by some other conventional electro-mechanical device so that the surface of the heart H as seen on the screen of the monitor 98 does not move. Alternatively, an electronic motion-compensator 95 may be interposed between the camera 90 and the monitor 98 which alters the TV signal to accomplish the same end. The motion compensator 95 may employ a signal from the mechanism 200 (for example, a variable resistor driven by the cam 230) or may employ internal circuitry to stop the image from moving vertically on the monitor 98. This could be accomplished, for instance, by placing a bright spot into the visual field and triggering the sweep of the monitor 98 to the bright spot; or by pattern recognition with triggering to some part of the pattern. A personal viewing device can be used instead of a monitor.

A fiber-optic imaging device of the type used in endoscopes (not shown), which sends images through fiber bundles to remote TV cameras, can be used in place of the full-size camera 90 of FIG. 8. Such a camera could be mounted alongside the tip 10 and oscillated in the same pattern OH as the tip 10, to stabilize the image. Also, a small mirror (not shown) could be similarly mounted alongside the tip 10 at an angle of about 45° to the axis of the handle 100. The artery A and needle N can then be viewed through a relatively long-focal-distance camera looking parallel to the axis of the handle 100.

Such camera arrangements can be doubled for stereo imaging of the operation, which can be useful for very fine suturing as the image will be magnified.

A lamp (not shown) may optionally be mounted on the handle 100 for illumination.

Figure 9A:
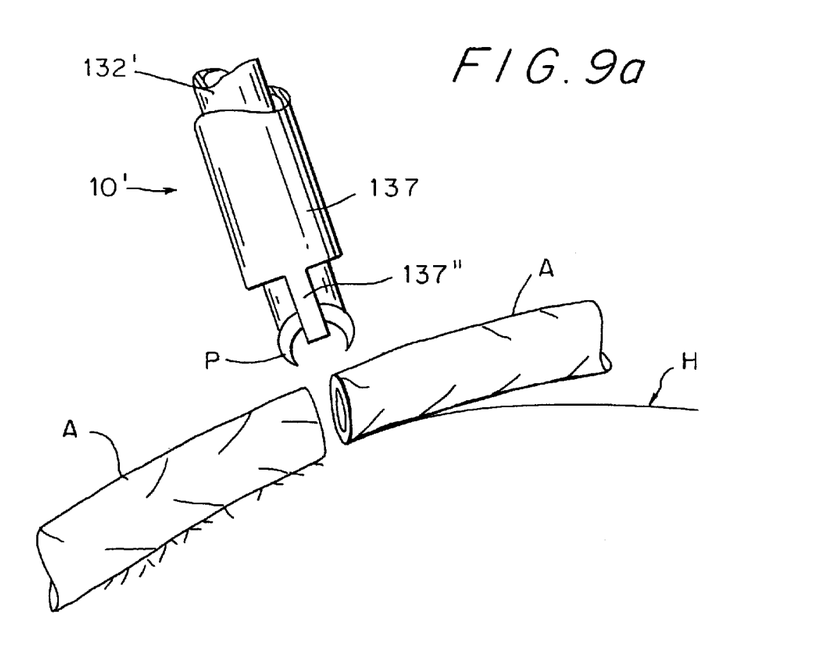
FIG. 9a shows a tip with a stapler.
Figure 9B:
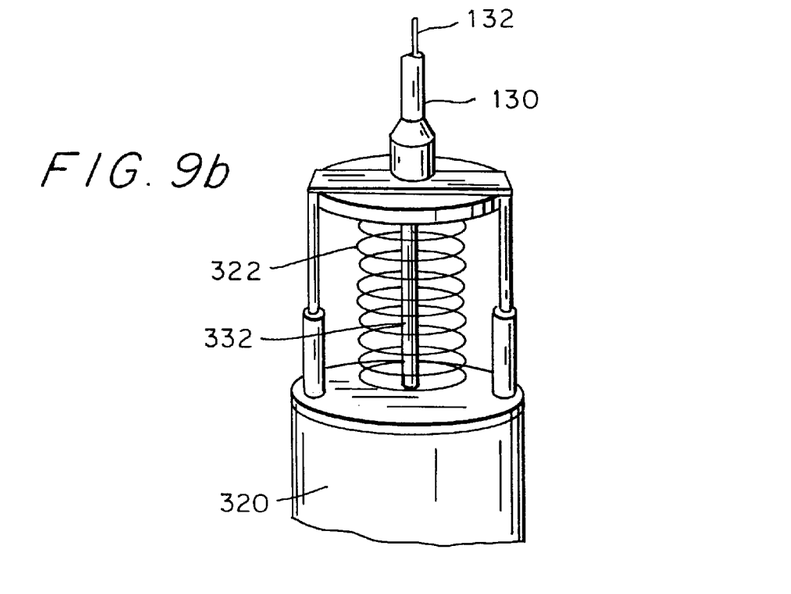
FIG. 9b is a perspective view of a solenoid for actuating the tip.

FIG. 9a illustrates a stapler tip 10' which is adapted to hold and crimp onto the artery A a staple P when the rigid portion 132' of the cable 130 moves downward, bending the staple P around the tube extension 137" and closing its pointed tips together through the wall of the artery A. FIG. 9b shows the solenoid 320, spring 322 and cable 130 which are also shown in FIG. 1. A rod 332, coupled to wire 132 of cable 130, pushes outward when the solenoid 320 is powered to compress the wire 132 and crimp the staple P of FIG. 9a. The spring 322 then retracts the wire 132. The wire 132 may also be placed into tension by activation of the solenoid 320 if the stapling tip is adapted to this. An hydraulic actuation for crimping the staple P (not shown) is also contemplated for the present invention.

The present invention also comprehends a tip with automatic staple feed and also all other conventional stapling apparatus or methods. Alternative tips (not shown) adapted to anastomosis with adhesives, light, heat, vibration, other mechanical fasteners, and so on, are within the scope of the invention, as well as tools adapted for operations other than anastomosis or arterial or venous repairs.

The present invention may be adapted to operations now performed as so-called "open-heart" surgery requiring a heart-lung machine and a stopped heart. The narrow tip 10 is able to protrude through a narrow incision in a large vein or artery wall or the heart itself, to work on valves and other internal structures while the heart is beating. The tip may be adapted to include a miniature endoscopic viewer in such cases, permitting "stopped-motion" imaging once the tip motion is correlated with the organ motion and for adjusting the motion of the tip. Since the tip motion includes lateral motion as well as reciprocating vector motion, a relatively complex motion like that of a heart valve may be duplicated by the present invention; and the provision of cam adjustment and/or selection permits varying the motion pattern during an operation. This may in the future permit operating on internal parts of the heart without the expense and danger of stopping the heart. In such operations the invention includes means for reducing blood leakage and for returning to the patient blood leaked through the narrow opening for the tip, for example by suctioning and then pumping the leaked blood to a vein.

The invention may also be adapted to virtually eliminate "twitching" of organs other than the heart, by incorporating a non-cyclical compensating motion activated in response to a twitch sensor. Such motion could be provided by the cam 230 and clutch 214 of FIG. 3, where the clutch was engaged by a twitch.

The invention is useful for any operation on a moving organ, and particularly for operations on the heart. The present invention may be adapted to any surgical tool and for any operation. As long as there is motivation to eliminate relative motion between a tool of any kind and an oscillating organ in a surgical setting, the apparatus of the present invention may be used.

The "means for causing reciprocation" is intended to encompass the disclosed mechanism, including the cam 230 as described herein, as well as all other mechanisms which will permit such reciprocation and are thus functionally equivalent to such a cam. Thus, once the intended function is known to those of ordinary skill in the art, many other mechanisms to accomplish the function can be designed and are intended to be part of the present invention. For example, the reciprocation may be caused by a piston driven by a computer so as to cause the arm 220 to oscillate at a predetermined programmed rate. Sensors to determine the relative amplitude, angle and pattern of the tip 10 as compared to the oscillating organ could feed input to the computer which would then feed back adjustments to the piston. While the illustrated means is simple and presently preferred, any other mechanism for accomplishing the specified function must be considered to be a functional equivalent to the illustrated cam.

The "means for synchronizing" the signalling of the pacer with the oscillation OH is preferably the illustrated switch 240 triggered by the actual movement of the mechanism. Again, however, any other mechanism for accomplishing this function is intended to be an equivalent to the illustrated mechanism. Thus, for example, if the movement of the tip 10 is computer controlled, the computer can also output the pacing signal. It is preferred that the same mechanism which drives the oscillation effectively drives the pacing of the heart.

The claimed means for adjusting one or more of the amplitude, phase or pattern of the oscillation is intended to encompass not only the illustrated mechanisms, but anything else that may be devised in order to accomplish this function. While a capacitance system for generating an auditory signal which varies as the distance varies, but becomes constant as the amplitude comes into alignment, is a simple and effective means for accomplishing this function, those of ordinary skill in the art can readily develop other means for accomplishing this function which are intended to be equivalent to the auditory mechanism disclosed. Thus, in a more complex computer driven system, the distance between the tip and the oscillating organ may be measured by other means, such as radar, sonar or laser type signals which display the relative distances on a computer output with the computer using this signal to adjust the amplitude of oscillation to maintain the distance constant.

The industrial applicability is in medical devices. The problem solved by the invention is motion of a moving organ to be operated on. The foregoing description of the specific embodiments will so fully reveal the general nature of the invention that others can, by applying current knowledge, readily modify and/or adapt for various applications such specific embodiments without undue experimentation and without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. The means, materials, and steps for carrying out various disclosed functions may take a variety of alternative forms without departing from the invention. Thus the expressions "means to . . . " and "means for . . . ", or any method step language, as may be found in the specification above and/or in the claims below, followed by a functional statement, are intended to define and cover whatever structural, physical, chemical or electrical element or structure, or whatever method step, which may now or in the future exist which carries out the recited function, whether or not precisely equivalent to the embodiment or embodiments disclosed in the specification above, i.e., other means or steps for carrying out the same functions can be used; and it is intended that such expressions be given their broadest interpretation.

What is claimed is:

1. An apparatus for supporting a surgical tool during a surgical operation on an organ, during which the organ is moving in an organ oscillation, the apparatus acting to cancel relative motion between the organ and the tool, the apparatus comprising in combination:
   a handle;
   a tip reciprocatingly movable relative to the handle, the tip including means for supporting a surgical tool; and
   means for causing reciprocation of said tip in a tip oscillation which is in synchronicity with the organ oscillation,
   whereby relative motion between the organ and the tip is at least partially canceled.

2. The apparatus in accordance with claim 1, wherein the oscillating organ is a heart and the organ oscillation is a heart oscillation, and further including:
   means for pacing the heart to beat in a constant rhythm, said means for pacing being connected to said means for causing reciprocation such that the constant rhythm set by said means for pacing is controlled by the tip oscillation, thereby maintaining synchrony of the tip oscillation and the heart oscillation.

3. The apparatus in accordance with claim 2, wherein said means for pacing includes having signals fed to the heart, which signals are triggered by the tip oscillation.

4. The apparatus according to claim 2, wherein said means for pacing causes the heart to beat faster than it would if not paced.

5. The apparatus in accordance with claim 1, further including means for adjusting one or more of the amplitude, phase or pattern of the tip oscillation to correspond to the organ oscillation.

6. The apparatus in accordance with claim 5, wherein said means for adjusting further includes means for sensing the relative amplitudes of oscillation of said tip and the organ.

7. The apparatus in accordance with claim 6, wherein said means for adjusting includes means for indicating a degree of difference between the tip oscillation and the organ oscillation.

8. The apparatus in accordance with claim 5, wherein said means for causing reciprocation comprises a rotary cam having a profile adapted to the pattern of the organ oscillation and an arm rotatably mounted on a hinge and driven by the cam to rotate about the hinge, and wherein said means for adjusting comprises means for moving said cam toward and away from said hinge.

9. The apparatus according to claim 5, wherein said means for adjusting causes adjustment of the oscillation amplitude of said tip.

10. The apparatus according to claim 5, wherein said means for adjusting causes adjustment of the oscillation phase of said tip.

11. The apparatus in accordance with claim 1, wherein said means for causing reciprocation comprises a rotary cam having a profile adapted to the pattern of the organ oscillation.

12. An apparatus for supporting a surgical tool during a surgical operation on an organ, during which the organ is moving in an organ oscillation, the apparatus acting to cancel relative motion between the organ and the tool, the apparatus comprising in combination:

a handle;

a tip including a surgical tool reciprocable relative to the handle; and a driving mechanism reciprocating said tip in a tip oscillation in synchronicity with the organ oscillation, whereby relative motion between the organ and the tip is at least partially canceled.

13. The apparatus according to claim 12, wherein the surgical tool is an anastomosis tool.

14. The apparatus according to claim 12, wherein the surgical tool is a stapler.

15. The apparatus according to claim 12, wherein the surgical tool is a needle holder.

16. The apparatus according to claim 15, wherein the oscillating organ is a heart and the organ oscillation is a heart oscillation, and further including:

a heart pacer to pace the heart in a constant rhythm, and, a synchronizer for synchronizing the tip oscillation and the heart oscillation.

17. The apparatus according to claim 12, wherein the surgical tool is operable by a remote device separated from the handle.

* * * * *